US006176234B1

(12) United States Patent
Salter et al.

(10) Patent No.: US 6,176,234 B1
(45) Date of Patent: Jan. 23, 2001

(54) MOUTHPIECE FOR A NEBULIZER

(75) Inventors: Peter W. Salter, Tehachapi; James Chua, Bakersfield; Walter Van Horn, Arvin; Duane D. Kazal, Tehachapi; Laurence McGann, Woodland Hills, all of CA (US)

(73) Assignee: Salter Labs, Arvin, CA (US)

( * ) Notice: Under 35 U.S.C. 154(b), the term of this patent shall be extended for 0 days.

(21) Appl. No.: 09/130,643

(22) Filed: Aug. 7, 1998

Related U.S. Application Data
(60) Provisional application No. 60/055,067, filed on Aug. 8, 1997.

(51) Int. Cl.[7] .............................. A61M 11/00; B05B 1/26

(52) U.S. Cl. ................................ 128/200.18; 128/200.14; 128/200.21; 128/203.12; 128/207.14; 128/863; 137/843; 137/844; 137/845; 137/849; 239/338; 239/370; 222/490; 222/491

(58) Field of Search ......................... 128/200.17, 200.18, 128/200.21, 200.23, 203.12, 203.16, 203.23, 204.14, 207.14, 863; 239/343, 338, 352, 370, 390, 396; 137/849, 845; 222/844; 490/845; 491/846, 850, 908, 859

(56) References Cited

U.S. PATENT DOCUMENTS

| | | | | |
|---|---|---|---|---|
| 236,719 | * | 1/1881 | Renton | 137/859 |
| 2,629,393 | * | 2/1953 | Langdon | 137/859 |
| 2,670,757 | * | 3/1954 | Delany | 137/859 |
| 2,785,923 | * | 3/1957 | Hickman | 239/338 |
| 2,908,283 | * | 10/1959 | Kiffer et al. | 137/859 |
| 3,176,712 | * | 4/1965 | Ramsden | 137/859 |
| 3,664,337 | * | 5/1972 | Lindsey et al. | 128/200.21 |
| 3,811,466 | * | 5/1974 | Ohringer | 137/493 |
| 4,198,969 | * | 4/1980 | Virag | 128/200.21 |
| 4,620,648 | * | 11/1986 | Schwartzman | 222/490 |
| 4,646,945 | * | 3/1987 | Steiner et al. | 222/207 |
| 4,907,581 | * | 3/1990 | King | 128/200.18 |
| 4,909,245 | * | 3/1990 | Wollenhaupt | 128/203.11 |
| 4,930,667 | * | 6/1990 | Holzner, Sr. | 222/189 |
| 5,117,999 | * | 6/1992 | Canzano et al. | 220/209 |
| 5,301,663 | * | 4/1994 | Small, Jr. | 128/200.18 |
| 5,324,267 | * | 6/1994 | DeWitt | 604/142 |
| 5,394,867 | * | 3/1995 | Swann | 128/201.25 |
| 5,453,097 | * | 9/1995 | Paradis | 604/247 |
| 5,584,285 | * | 12/1996 | Salter et al. | 128/200.21 |
| 5,666,945 | * | 9/1997 | Davenport | 128/200.14 |
| 5,782,232 | * | 7/1998 | Rowland | 128/200.14 |
| 5,875,774 | * | 3/1999 | Clementi et al. | 128/200.18 |

FOREIGN PATENT DOCUMENTS

| | | | | |
|---|---|---|---|---|
| 2124519 | * | 11/1994 | (CA) | 128/200.21 |
| 2143599 | * | 3/1973 | (DE) | 604/58 |
| 0626180A1 | * | 11/1994 | (EP) | 128/200.21 |
| WO 86/01731 | * | 3/1986 | (WO) | 128/200.21 |

* cited by examiner

*Primary Examiner*—John G. Weiss
*Assistant Examiner*—Joseph F. Weiss, Jr.
(74) *Attorney, Agent, or Firm*—Davis and Bujold

(57) ABSTRACT

A mouth piece exhalation valve for a nebulizer or breathing circuit. The nebulizer has an internal passageway containing an offset causing an inspiration mist flow to bypass the exhaust valve without impingement. The offset includes a deflector which aids in the deflection of the inspiration mist flow away from the exhaust valve. The deflector is also utilized for directing the exhaust flow upon expiration by a patient through the exhaust valve. The exhaust valve design includes a flap or disc having leaves formed by peripheral arcuate cuts to facilitate the opening and the closing of the leafs in accordance with the expiration and inhalation of a patient respectively. The cuts also aid in the re-introduction of any accumulation of fluid on the external surface of the disc and valve back into the inspirational cycle so as to minimize any external buildup of fluid.

10 Claims, 5 Drawing Sheets

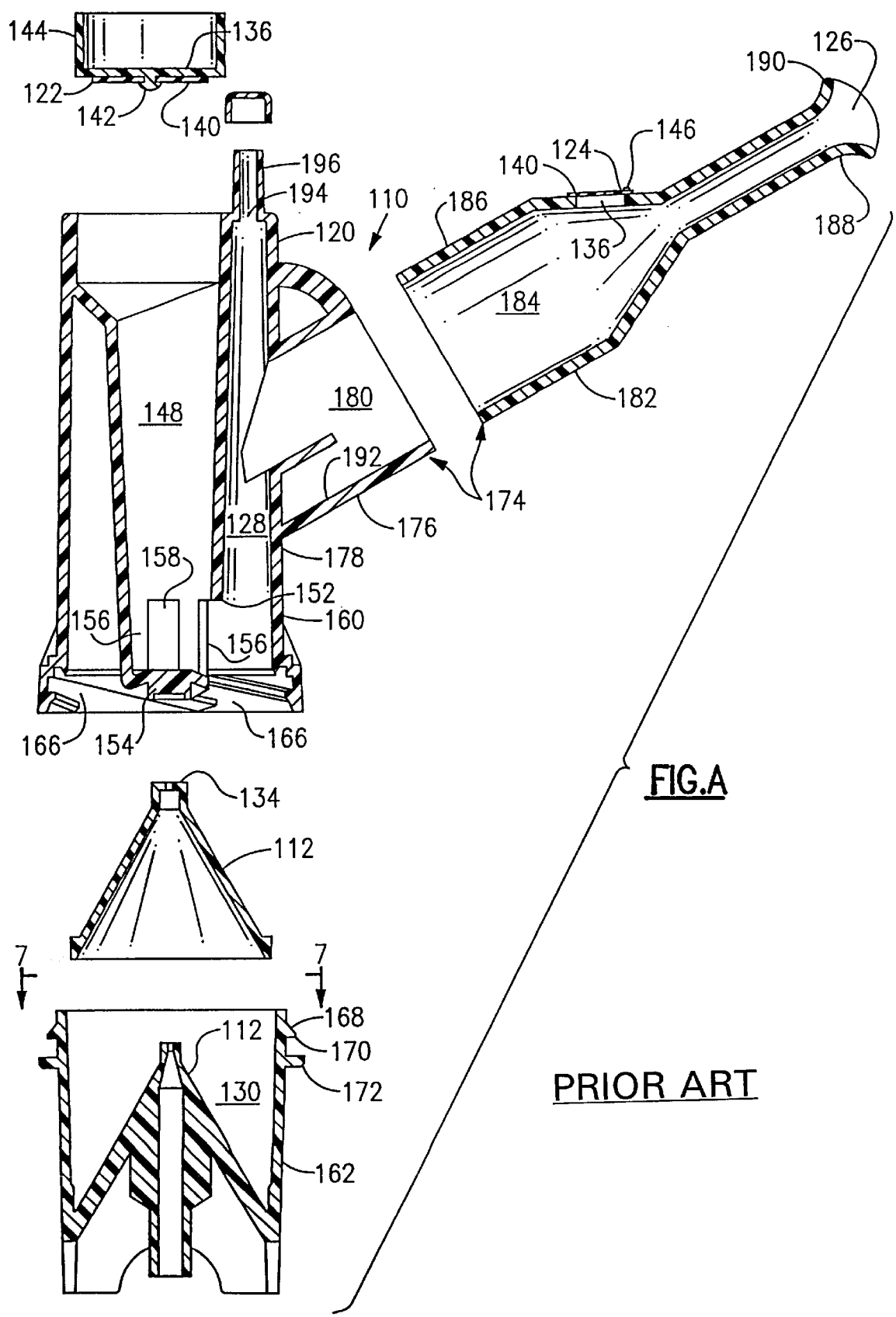

MOUTHPIECE FOR A NEBULIZER

This application is claiming priority from U.S. Provisional application Ser. No. 60/055,067, filed Aug. 8, 1997.

FIELD OF THE INVENTION

This invention relates to an improved mouthpiece for a nebulizer.

DESCRIPTION OF THE PREVIOUSLY PUBLISHED ART

Figure 1:
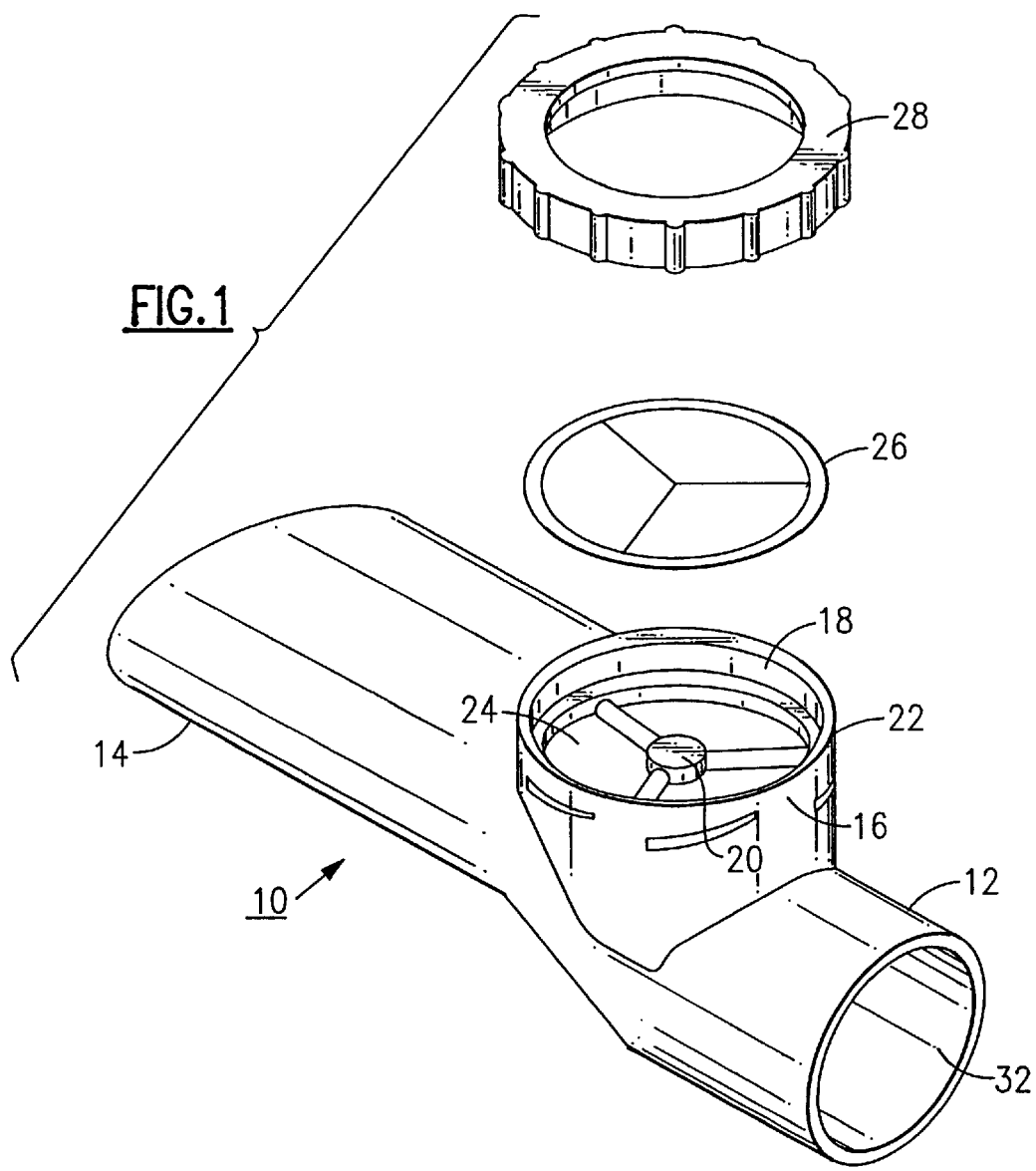
Figure 3:
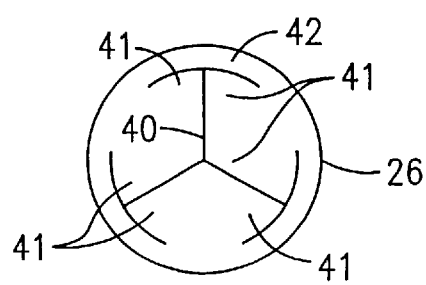

Our earlier U.S. Pat. No. 5,584,285, the entire contends of which are incorporated herein by reference, discloses a nebulizer with a mouthpiece having a flap valve 124 shown in FIG. 3 of the patent which is reproduced here as FIG. A. When the patient exhales into the mouthpiece 126 the air pressure causes the flap 124 to open and let the exhaust air out of the mouthpiece.

This early design, while operational and commercially effective, is not optimal. Since the flap valve 124 is in the path of the incoming inspiration mist, there is the possibility that the mist under sufficient pressure can cause the flap to slightly open such that some of the mist will leave the mouthpiece in the form of rainout before it reaches the patient. When the patient exhales, there is no structure to direct the exhaust flow against the valve or increase back pressure to assist the valve opening. The valve only opens when the exhaust gas back pressure reaches a certain level. The flap valve is made of a stiff yet flexible material and thus it will inherently have some resistance to open at vary low pressures. If any rainout accumulates on the external surface of the flap valve, it is also difficult for the liquid material to flow back into the mouthpiece. The inner peripheral surface of the flap may stick to the overlapping external surface of the mouthpiece when the inner surface of the flap is wet.

OBJECTS OF THE INVENTION

It is an object of this invention to provide an improved mouthpiece exhalation valve for a nebulizer or breathing circuit containing a nebulizer where the design of the internal passageway contains an offset which causes the inspiration mist flow to bypass the exhaust valve without infringement.

It is a further object of this invention to provide an improved mouthpiece for a nebulizer where a deflector aids in the flow control on inspiration so as to further deflect away the inspiration mist from the exhaust valve.

It is a further object of this invention to provide an improved mouthpiece for a nebulizer where a deflector is utilized to directing the exhaust flow on expiration through the exhaust valve.

It is a further object of this invention to provide an improved mouthpiece for a nebulizer where the exhaust valve is a valve disc with radial cuts to form leaves which open upon exhalation.

It is an object of this invention to provide an improved mouthpiece for a nebulizer where the exhaust value is in the form of a disc with leaves that have peripheral arcuate cuts at the root of leaves to reduce stiffness and facilitate their opening.

It is a further object of this invention to provide an improved mouthpiece for a nebulizer with an exhaust value in the form of a disc which opens and where the disc is maintained in a disc housing.

It is a further object of this invention to provide an improved mouthpiece for a nebulizer where an exhaust disc valve is maintained in a disc housing by a removable press fitted retainer ring which allows for removal of the valve disc for cleaning.

It is a further object of this invention to provide an improved mouthpiece for a nebulizer where the retainer ring for the disc housing has external bumps or projections for better finger gripping to aid in its removal.

It is a further object of this invention to provide an improved mouthpiece for a nebulizer with an exhaust valve in the form of a disc valve having cuts so that any accumulation of fluid on external surface will be able to be sucked back inside during the inspiration cycle so as to minimize external buildup of liquid.

It is a further object of this invention to provide an improved mouthpiece for a nebulizer where the exhaust value is in the form a disc valve positioned on support grille arms which have narrow top surfaces to minimize sticking of the valve elements to the support arms upon exhalation.

It is a further object of this invention to provide an improved mouthpiece for a nebulizer where the mouthpiece has an oval shaped mouth end that is anatomical so as to better fit in the patents' mouth.

It is a further object of this invention to provide an improved mouthpiece for a nebulizer which is easier to produce because both the mouth end and the nebulizer connecting end have straight-pull core pieces which facilitate easy construction of the mold die.

It is a further object of this invention to provide an improved mouthpiece for a nebulizer.

These and further objects of the invention will become apparent as the description of the invention proceeds.

BRIEF DESCRIPTIONS OF THE DRAWINGS

FIG. A is a portion of an exploded side view in cross-section of a prior published mouthpiece and a portion of the nebulizer.

FIG. 1 is an exploded perspective view of the mouthpiece.

FIG. 2 is a cross-sectional side view of the mouthpiece.

FIG. 3 is a top view of the valve disc with peripheral and radial cuts.

FIG. 4 is a side view of the mouthpiece without the retaining ring.

FIG. 5 is a top view of the mouthpiece without the retaining ring and the valve disc.

FIGS. *6a*, *6b*, *6c*, *6d* illustrates various cut patterns for the valve disc.

FIGS. *7a* and *7b* illustrates alternative valve support embodiments.

DETAILED DESCRIPTION OF THE INVENTION

The improved mouthpiece device according to the invention can be described by referring to the perspective view shown in FIG. 1. The mouthpiece 10 has a circular connector piece 12 which engages the outlet of the nebulizer in the same way that the mouthpiece engages the nebulizer in FIG. A. The opposite end of this mouthpiece device is the mouth shaped end piece 14 that his placed in the patient's mouth. On top is the valve disc housing 16 that holds the exhaust valve for exhausting the exhalation from the patient. In this exploded view the valve housing 16 contains an inner ring 18 at the base which serves as a support ring for hte valve disc. In the embodiment illustrated there is a central hub 20 which is supported by three grille arms 22. These grille arms are quite thin so that the open areas 24 between them represent a substantial portion of the cross-sectional area in the housing. Other configurations and different numbers of arms can be used. Above the housing in the exploded view is the valve disc 26 that will fit down on top of the grille arms and the support ring 18. Above the valve disc in the exploded view is the retainer ring 28 having the outer wall shown and a second inner wall not shown which is of just a slightly smaller diameter. The two concentric walls snap fit over the valve housing wall 16 to keep the outer peripheral area of the valve disc in place when the unit is assembled. The retaining ring 18 has a series of projections or ribs 20 to facilitate gripping the ring and twisting it off to remove it.

Figure 2:
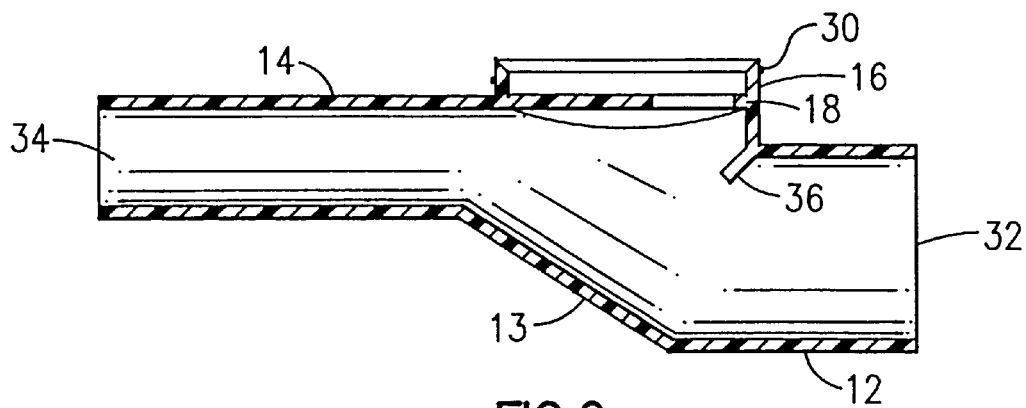
Figure 5:
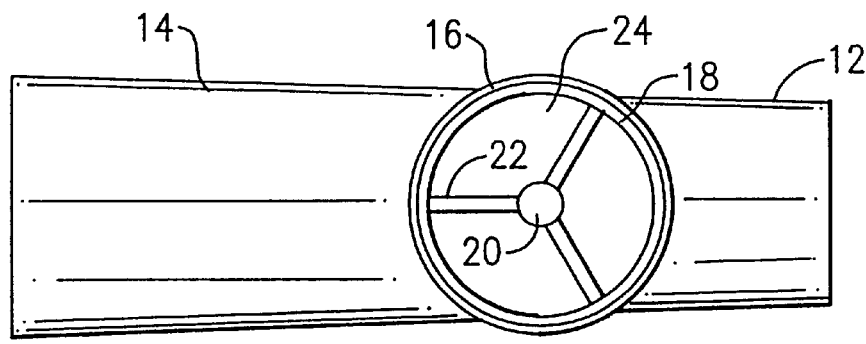
Figure 4:
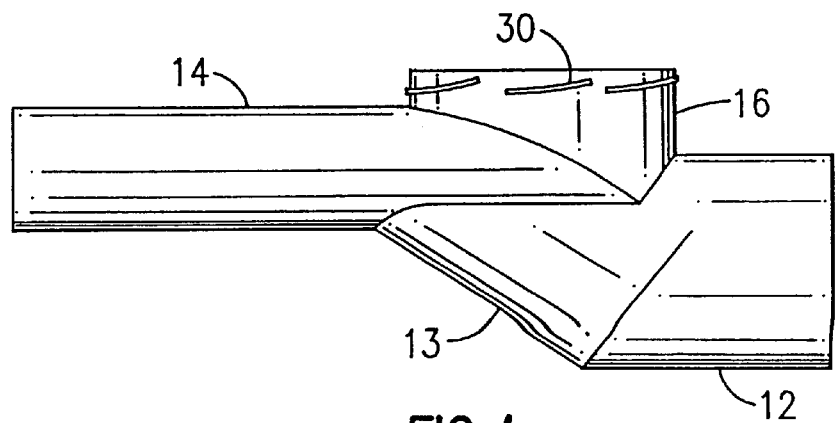
Figure 6A:
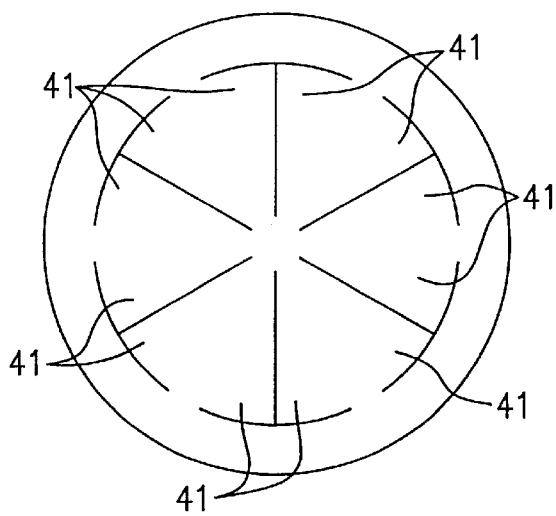
Figure 6B:
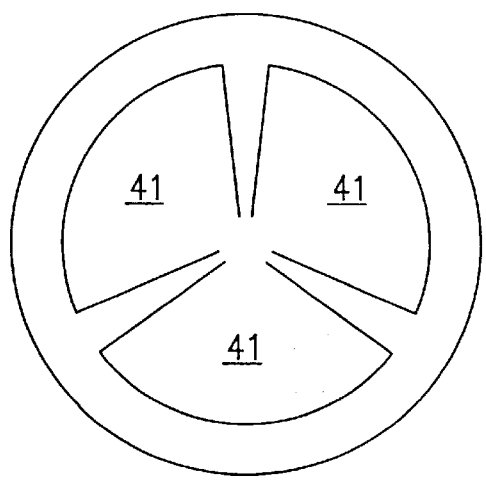
Figure 6C:
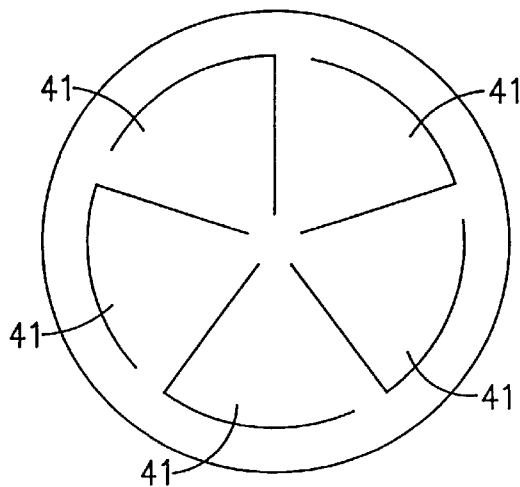
Figure 6D:
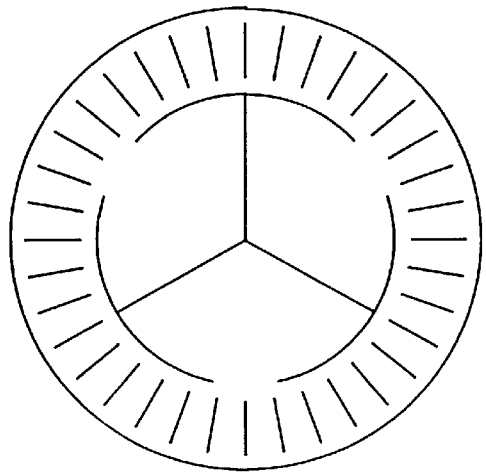
Figure 7A:
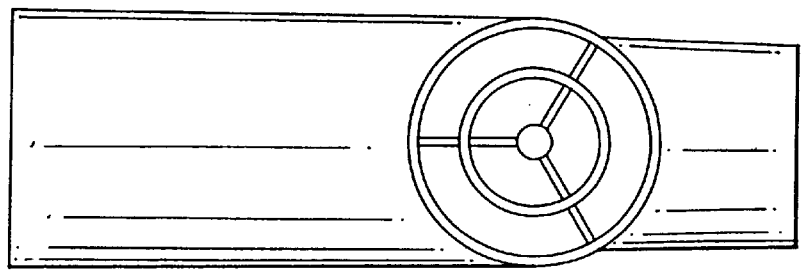
Figure 7B:
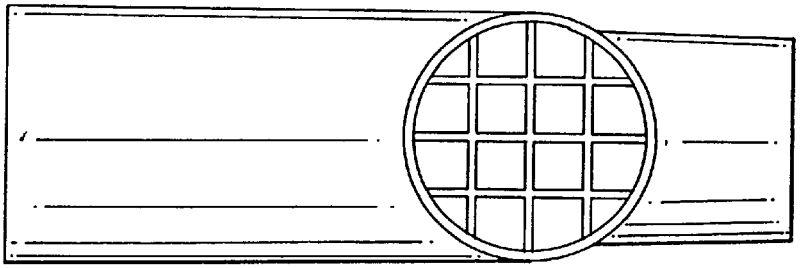

FIG. 2 is a cross-sectional side view of the mouthpiece device showing the elevational relationship of the parts and passageways. The retaining ring 28 has been removed as has the valve disc for better clarity. The circular connector 12 will fit into the conventional circular outlet port of nebulizer. The mouth shaped end piece 14 at the other end is positioned above the center line of the circular connector 12. The back wall 13 of the connector 12 joins the connector to the upper mouthpiece. The valve housing 16 is part of the mouth shaped end piece 14. Inside the housing the support ring 18 is shown as well as the hub and support arm. When the mouthpiece s used by the patient, the inspiration mist enters the circular connector 12 through its opening 32 and passes through the device and out the opening 34 in the mouthpiece. In that flow path inside the circular connector 12 is a deflector 36 which extends out at an obtuse angle from the inside wall of the circular connector 12. The purpose of the deflector is two fold. First, with regard to the incoming inspiration mist, the deflector deflects that gas stream away from the valve disc in the valve housing above so that the mist will not strike the valve disc and thus there is no possibility that some of the mist might leave through the valve disc. The second function is that in the respiration cycle when the patient is exhaling, the exhalation gas will be coming down the passageway 34 and the deflector deflects that exhalation gas up into the valve housing 16 where it can exhaust through the valve disc 26.

FIG. 3 is a top view of the thin valve disc. There can be many possible cut patterns in the disc so that it defines various flaps which will open upwardly when the exhalation pressure is applied to permit the exhalation gas to leave the mouthpiece. Seen here are three radial cuts 40 from the center and three peripheral cuts 42 which define 6 flaps. As exhalation gas pressure is applied from below, these 6 flaps will open up along the cut lines to let the gas escape.

FIG. 4 is an outside view of the device showing again the elevational relationship between the circular connector 12, its back wall 13 connecting to the higher level mouth shaped end piece 14. The valve housing is made a part of the mouth shaped end piece 16 above where it connects to the circular connector.

FIG. 5 is a top view of the device with the retaining ring 29 removed as well as the valve disc. The support structure for the valve disc is made up of the inner ring surface 18, the three grille arms 22 and the central hub 20. The end of the mouth shaped piece that is placed in the patient's mouth has a wider width than the opposite end where the valve housing is located. The mouth end is designed to have an oval opening and to better anatomically fit in the patient's mouth.

FIG. 6 illustrates various alternative cut patterns for the valve disc 44. In **6*a* each of the radial cuts toward the center form a flap on either side of the cut in conjunction with the peripheral cuts so there will be 12 flaps which can open up in response to the exhalation pressure. In 6*b* there are 3 large flaps which pivot about the center and extend up from the periphery. In 6*c* where each radial cut meets the peripheral cut it forms the apex for a flap. Thus here are 5 flaps formed. In 6*d* each radial cut defines two flaps and so there will be 6** flaps formed.

FIGS. **7*a*, 7*b*** are plan views of alternative support means integral with the hollow mouthpiece element positioned so as to prevent the opening of the exhaust valve element during patient or user inhalation.

It is understood that the foregoing detailed description is given merely by way of illustration and that many variations may be made therein without departing from the spirit of this invention.

What is claimed is:

1. A mouthpiece device for inspiration of a mist from a nebulizer comprising:

an inlet connector adapted to engage an outlet port of the nebulizer;

a hollow mouthpiece for insertion into a patient's mouth;

a conduit forming a fluid passageway between the inlet connector and the hollow mouthpiece;

an exhaust valve for removing exhalation gases and fluids exhaled into the mouthpiece device, to outside the device, said exhaust valve being positioned on the conduit between the inlet connector and the hollow mouthpiece;

exhaust valve support means positioned below, when in use, and in contact with a valve disc and integral with the hollow mouthpiece so as to prevent opening of said exhaust valve during patient inhalation; and a deflector positioned in the conduit between the exhaust valve and the inlet connector to deflect inspiration mist flowing into the inlet connector away from the exhaust valve, and to deflect exhalation gases emanating from the hollow mouthpiece toward the exhaust valve;

wherein the exhaust valve comprises a valve disc housing securing an annular outer peripheral edge portion, in its entirety, of the valve disc between a support ring and a retaining ring, the valve disc having a plurality of radial cuts, each radial cut being joined with a circumferential cut arranged adjacent the peripheral edge and radially inward of the secured edge portion, to form a plurality of hingeable flaps facilitating the opening of the valve in response to pressure in the fluid passageway resulting from exhalation therethrough by a patient and return of rainout exhausted through the exhaust valve to the fluid passageway of the mouthpiece.

2. The mouthpiece device according to claim 1, wherein said circumferential cuts are arcuate circumferential cuts and circumferentially closely spaced.

3. The mouthpiece device according to claim 1, wherein the exhaust valve support means are thin support elements positioned under the disc to prevent an inward opening of said hingeable flaps of the exhaust valve disc during patient inhalation and enable the hingeable flaps to open outwardly upon patient exhalation.

4. The mouthpiece device according to claim 1, wherein, when in use the inlet connector is positioned below the hollow mouthpiece and the conduit extends upwardly from the inlet connector to the hollow mouthpiece.

5. The mouthpiece device according to claim 4, wherein, when in use, the deflector is positioned in conduit in a region where the conduit extends upwardly from the inlet connector to the hollow mouthpiece.

6. The mouthpiece device according to claim 1, wherein the plurality of radial cuts have a common radially inner end point located substantially centrally on the valve disk.

7. The mouthpiece device according to claim 1, wherein a radially outer end of each radial cut joins a circumferential cut intermediate opposed ends of that circumferential cut.

8. The mouthpiece device according to claim 1, wherein a radially outer end of each radial cut is joined with a circumferential cut at an end of that circumferential cut.

9. The mouthpiece according to claim 8, wherein each opposed end of each circumferential cut is joined with a said radial cut.

10. The mouthpiece device according to claim 1, wherein the radially inner ends of the radial cuts are separated and terminate adjacent the center of the valve disk.

* * * * *